(12) United States Patent  
Morrison et al.

(10) Patent No.: US 8,038,652 B2
(45) Date of Patent: Oct. 18, 2011

(54) BUTTON CANNULA

(75) Inventors: David S. Morrison, Long Beach, CA (US); Peter J. Dreyfuss, Naples, FL (US); Thomas Dooney, Jr., Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 12/396,009

(22) Filed: Mar. 2, 2009

(65) Prior Publication Data

US 2009/0221968 A1    Sep. 3, 2009

Related U.S. Application Data

(60) Provisional application No. 61/032,872, filed on Feb. 29, 2008, provisional application No. 61/111,214, filed on Nov. 4, 2008.

(51) Int. Cl.
*A61M 5/178* (2006.01)
(52) U.S. Cl. .................................................. 604/164.11
(58) Field of Classification Search .................. 600/184, 600/206, 207, 208; 606/108, 213, 191, 248, 606/249; 604/96.01, 158, 164.01, 533, 192, 604/178, 104, 103.03, 910, 117, 23, 174
See application file for complete search history.

(56) References Cited

U.S. PATENT DOCUMENTS

| 3,856,021 | A  |   | 12/1974 | McIntosh |
| 4,809,679 | A  | * | 3/1989  | Shimonaka et al. .......... 600/154 |
| 5,545,179 | A  | * | 8/1996  | Williamson, IV ............ 606/213 |
| 5,916,198 | A  | * | 6/1999  | Dillow ....................... 604/167.04 |
| 6,033,426 | A  | * | 3/2000  | Kaji ............................... 606/213 |
| 6,276,661 | B1 | * | 8/2001  | Laird ........................... 251/61.1 |
| 6,440,063 | B1 |   | 8/2002  | Beane et al. |
| 2006/0030755 | A1 |   | 2/2006  | Ewers et al. |

FOREIGN PATENT DOCUMENTS

| DE | 3002298 A1 | 7/1981 |
| EP | 2-044-889 A1 | 4/2009 |
| WO | WO 2004/075730 | 9/2004 |
| WO | WO 2006/110733 | 10/2006 |

* cited by examiner

*Primary Examiner* — Christopher D Koharski
(74) *Attorney, Agent, or Firm* — Dickstein Shapiro LLP

(57) ABSTRACT

Flexible button cannulas for arthroscopic surgery made from silicone, or a similar flexible material. Exemplary embodiments of the button cannula have large inner and outer flanges for improved stability when installed into the body. Exemplary embodiments of the button cannula include two fluid dams. A first dam is located within the cannula elongated portal between the inner and outer flanges and prevents fluid from squirting out of the body when instruments are being inserted through the cannula. A second dam is located at the outer, or top, flange (i.e., the flange that remains outside of the body) to prevent fluid from squirting when the cannula itself is being inserted within the body. Exemplary embodiments of the button cannula also include an outer, or top, flange that is thicker than the inner, or bottom, flange, to prevent the over insertion of the cannula into the body.

12 Claims, 4 Drawing Sheets

BUTTON CANNULA

CROSS-REFERENCE TO RELATED APPLICATIONS

This application claims the benefit of U.S. Provisional Application No. 61/032,872, filed Feb. 29, 2008, and of U.S. Provisional Application No. 61/111,214, filed Nov. 4, 2008, the entire disclosures of which are incorporated by reference herein.

FIELD OF THE INVENTION

The present invention relates to cannulas having inner and outer flanges separating a portal for allowing various surgical instruments to be introduced in the body.

BACKGROUND OF THE INVENTION

Cannulas are generally used in endoscopic surgical procedures which enable closed surgery to be performed via portals. A variety of elongated instruments may be passed through the portals to gain access to an internal surgical work site (e.g., a knee, a shoulder, etc). Very often a disposable cannula is inserted into the portal in order to provide a convenient passageway through which various instruments may pass.

Because many arthroscopic procedures require the use of pressurized fluid to distend and irrigate the joint being operated upon, the cannula must provide a sealed passageway in order to enable instruments to be passed into and out of the cannula while maintaining a fluid seal to prevent squirting whether or not an instrument is in the cannula passageway. The sealing of such cannula passageways is usually accomplished by one or more membranes attached to the proximal end of the elongated cannula.

Some prior art devices utilize two different sealing mechanisms: one optimized for sealing when no instrument is present in the cannula and another optimized for sealing while an instrument is present.

Prior art cannulas are also generally rigid and inflexible, and since the portals through which endoscopic surgery is performed are desired to be as small in diameter as possible, the inner flanges of such cannulas are generally not wide enough to provide the optimum amount of stability while instruments are being transferred therethrough. Accordingly, there is a need in the art for an improved cannula with a wider and more stable inner flange. There is also a need for a cannula that can be inserted into the body using a minimally invasive insertion tool through a portal. Further, there is a need in the art for a cannula that has two fluid seals, or dams; a first dam to prevent fluid from squirting from within the body when instruments are passing through the cannula, and a second dam to prevent fluid from squirting when the cannula is being inserted within the portal. A cannula designed with a stop gap measure to prevent the possibility of over insertion in the body is also needed.

SUMMARY OF THE INVENTION

The present invention provides a flexible button cannula for arthroscopic surgery made from silicone, or a similar flexible material. Exemplary embodiments of the button cannula have large inner and outer flanges for improved stability when installed into the body. Further, exemplary embodiments of the button cannula include two fluid dams. A first dam is located within the cannula elongated portal between the inner and outer flanges and prevents fluid from squirting out of the body when instruments are being inserted through the cannula. A second dam is located at the outer, or top, flange (i.e., the flange that remains outside of the body) to prevent fluid from squirting when the cannula itself is being inserted within the body. Exemplary embodiments of the button cannula also include an outer, or top, flange that is thicker than the inner, or bottom, flange, to prevent the over insertion of the cannula into the body.

Other features and advantages of the present invention will become apparent from the following description of the invention, which refers to the accompanying drawings.

DETAILED DESCRIPTION OF PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention is a flexible button cannula for arthroscopic surgery made from silicone, or a similar flexible material. Exemplary embodiments of the button cannula have large inner and outer flanges for improved stability when installed into the body. Further, exemplary embodiments of the button cannula include two fluid dams. A first dam is located within the cannula elongated portal between the inner and outer flanges and prevents fluid from squirting out of the body when instruments are being inserted through the cannula. A second dam is located at the outer, or top, flange (i.e., the flange that remains outside of the body) to prevent fluid from squirting when the cannula itself is being inserted within the body. Exemplary embodiments of the button cannula also include an outer, or top, flange that is thicker than the inner, or bottom, flange, to prevent the over insertion of the cannula into the body.

Figure 1:
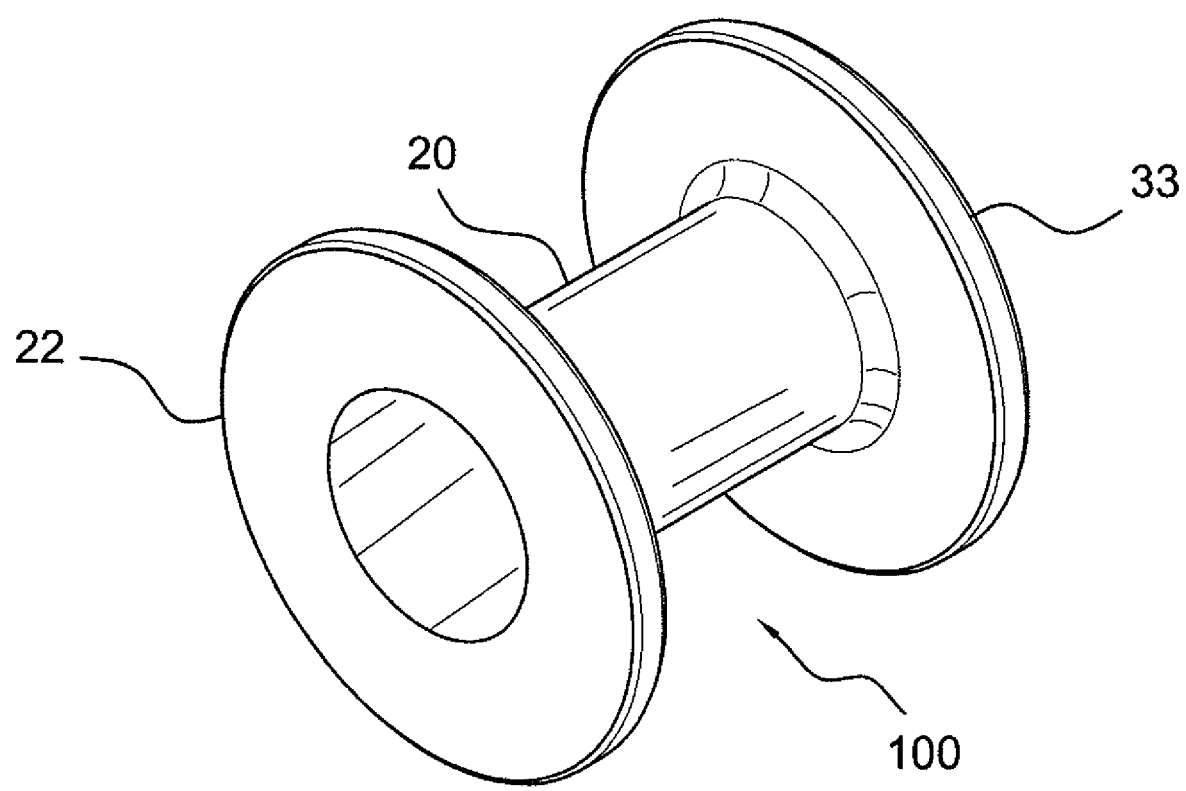
FIG. 1 illustrates a perspective view of a button cannula in accordance with a first embodiment of the invention.
Figure 2:
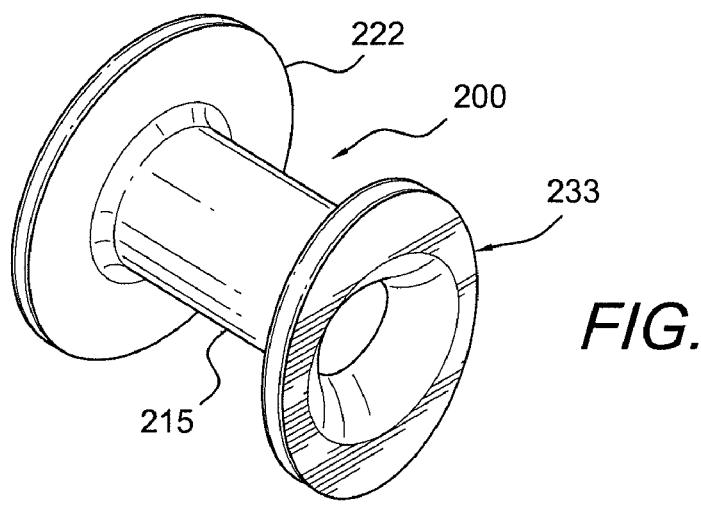
FIG. 2 illustrates a perspective view of a button cannula in accordance with a second embodiment of the invention.
Figure 3:
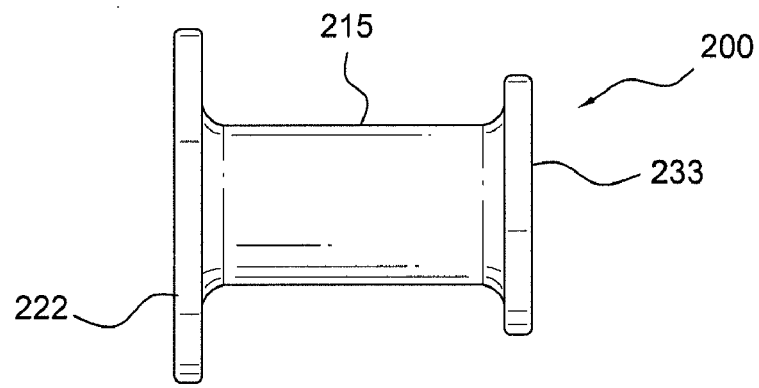
FIG. 3 illustrates a side view of the button cannula of FIG. 2.
Figure 4:
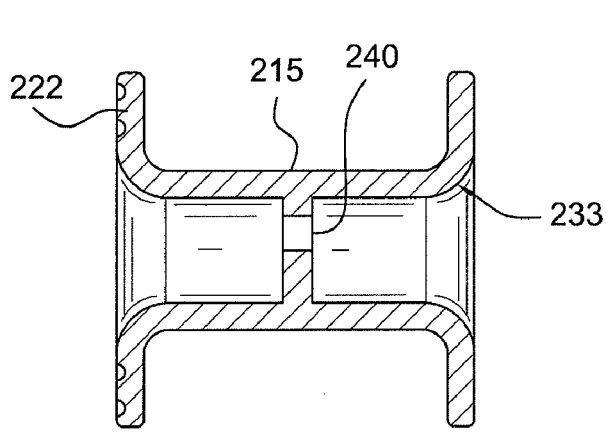
FIG. 4 illustrates a cross-sectional view of the button cannula of FIG. 2.
Figure 5:
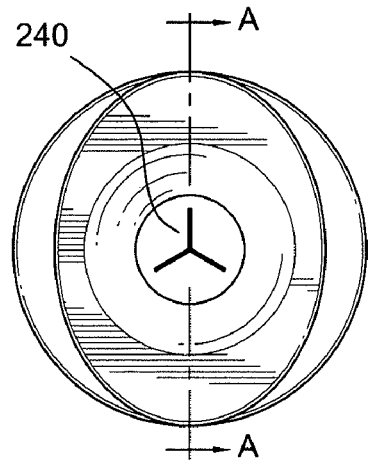
FIG. 5 is a top view of button cannula of FIG. 4.

Referring now to the drawings, where like elements are designated by like reference numerals, FIGS. 1-10 illustrate exemplary embodiments of the button cannula 100, 200, 300 of the present invention. FIG. 1 illustrates flexible button cannula 100 that includes two deformable lips or flanges (two flip ears), an inner deformable lip and an outer deformable lip. For example, button cannula 100 includes an outer, or top, flange 22 and an inner, or bottom, flange 33, with a portal 20 extending therebetween. The flanges are integral with portal 20.

In accordance with an exemplary embodiment of the invention, the cannula 100 is manufactured from a flexible material (e.g., silicone) which enables the cannula to be deformed and/or otherwise condensed in size and inserted into an insertion tool (not shown). In exemplary embodiments, the flanges may be formed of a same material as that of the portal 20, or may be formed of a different material. Preferably, all components of the cannula 100 are formed of a flexible material (e.g., silicone). Once installed into the body, the inner flange 33 expands to its original shape and maintains the cannula in position.

FIGS. 2-5 illustrate another exemplary embodiment of a button cannula 200 which is similar in part to the cannula 100 of FIG. 1, but differs in that cannula 200 includes an inner, or lower, flange 233 that is oval in shape and an outer, or top, flange 222 that is circular in shape. In accordance with an exemplary embodiment, the inner flange 233 is oval in shape so that when two or more button cannulas are deployed close together (e.g. for instability cases in the joint space), the inner, oval flanges 233 can be oriented so that the minor diameters of the ovals would be adjacent to each other, and therefore not overlap as much as would circular flanges.

Button cannula 200 also differs from the cannula 100 of FIG. 1 in that cannula 200 includes a dam 240 (FIG. 4) which is located in portal 215 (FIG. 3) at approximately the mid-point between the outer flange 222 and the inner flange 233. The dam 240 prevents fluid from squirting from within the body when instruments are being inserted through the portal 215 and also when no instruments are inserted through the portal 215. The dam 240 is formed by slits in the flexible material.

FIGS. 6-9 illustrate another exemplary embodiment of button cannula 300 of the present invention. Button cannula 300 is similar in part to the cannula 100 (FIG. 1) and cannula 200 (FIGS. 2-5), but differs from them in that cannula 300 includes an outer flange 322 that is thicker than the inner flange 333. The thicker outer flange 322 helps prevent over-insertion of the cannula 300 during the insertion process by virtue of the thicker outer flange 322 being more difficult to pass through the portal and into the body as compared with the inner flange 333. In an exemplary embodiment only, the thickness of the outer flange 322 is about twice the thickness of the inner flange 333. Each of the outer flange 322 and the inner flange 333 may be circular or oval in shape, and may have similar or different diameters.

Figure 6:
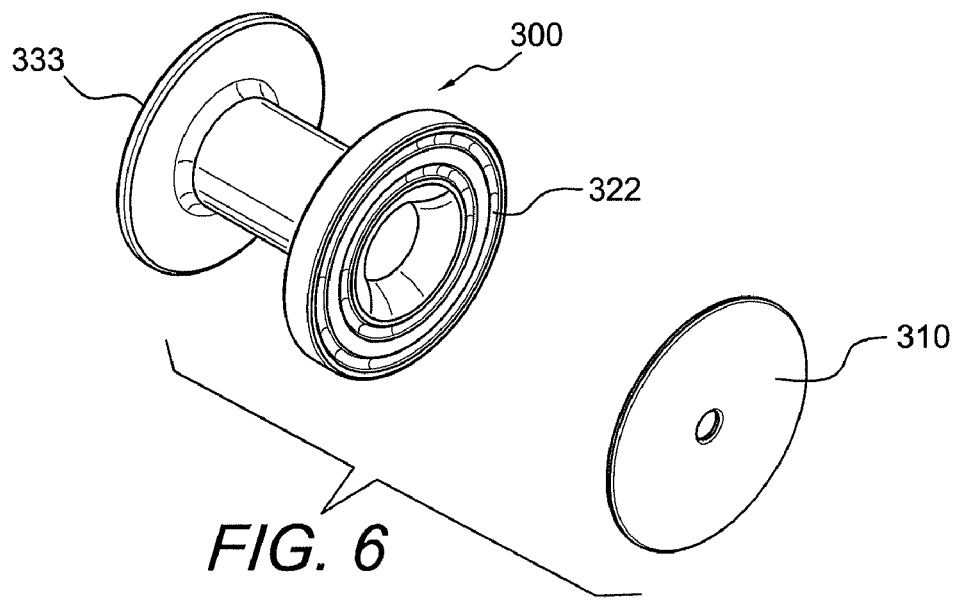
FIG. 6 illustrates an expanded, perspective view of a button cannula in accordance with a third embodiment of the invention.
Figures 7, 8:
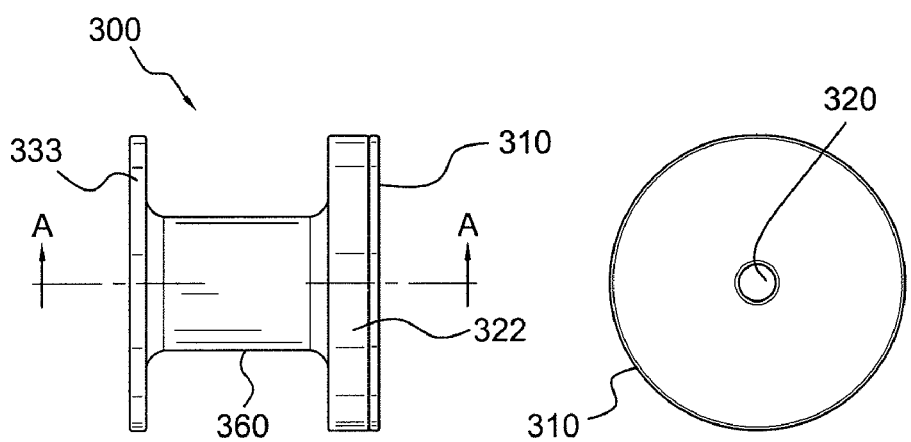
FIG. 7 illustrates a side view of the button cannula of FIG. 6.
FIG. 8 is a top view of button cannula of FIG. 4.
Figure 9:
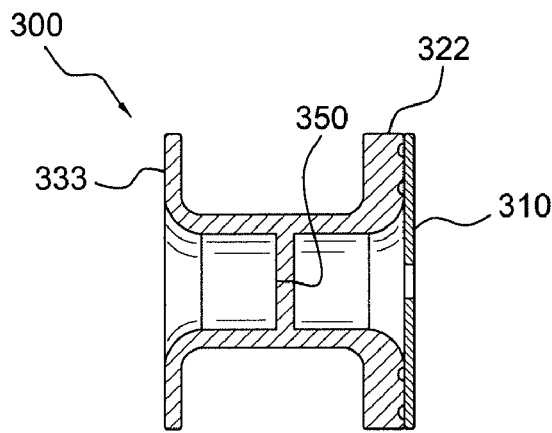
FIG. 9 illustrates a cross-sectional view of the button cannula of FIG. 7, taken along section A-A in FIG. 7.

FIG. 6 also depicts a second outer flange 310 to be affixed to the first outer flange 322 (as shown in FIG. 7, for example). The second outer flange 310 includes a dam 320 in the form of a small hole for preventing fluid from squirting from within the body during insertion of the cannula 300. FIG. 9 illustrates a second dam 350 located within portal 360 of cannula 300, at approximately the mid-point between the inner flange 333 and the outer flange 322.

Figure 10:
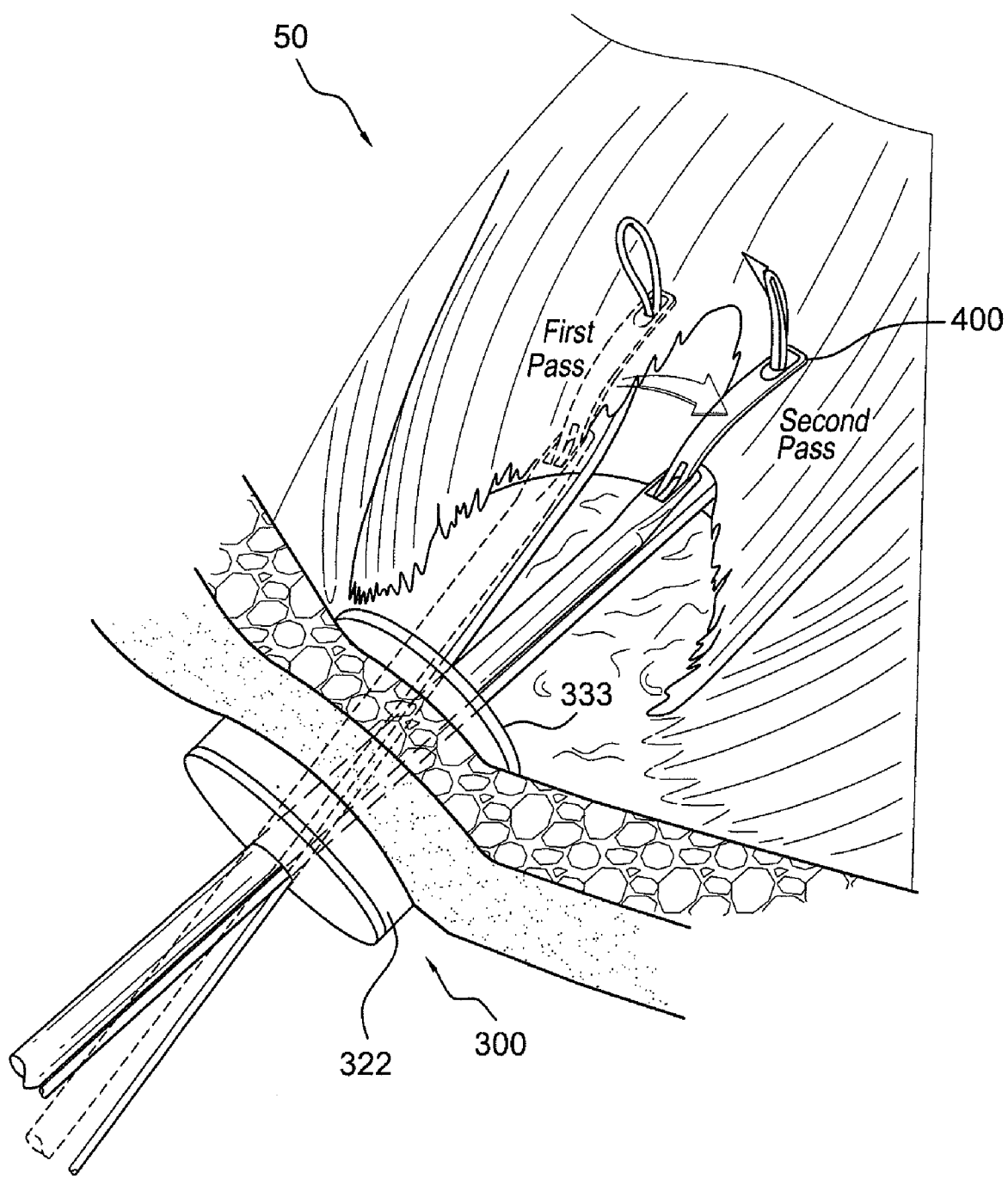
FIG. 10 illustrates the button cannula of FIG. 6 employed during an arthroscopic rotator cuff repair, and in accordance with a method of conducting surgery of the present invention.

FIG. 10 illustrates button cannula 300 of FIGS. 6-9 depicted in use, and in accordance with an exemplary embodiment of the invention. The button cannula 300 is depicted as being inserted within a portal formed in the body and adjacent an arthroscopic repair site 50 (which may be a shoulder joint undergoing a rotator cuff repair, for example). The inner flange of cannula 300 is depicted as being within the body and the outer flange 322 is depicted as being outside of the body. The outer flange 322 is depicted as being thicker than the inner flange 333 for reasons described above. As depicted, arthroscopic or endoscopic instruments (for example, a suture passing instrument 400 shown in FIG. 10) are passed through the button cannula 300 from outside of the body to inside the body.

As known in the art, during insertion through a surgical portal, the cannula 100, 200, 300 may be slidably moveable relative to a cylindrical sleeve (or outer tube). When the cannula 100, 200, 300 is inserted through the tube (for example, a corresponding cylindrical sleeve or outer tube), the inner and outer deformable flanges collapse, to allow insertion of the cannula through the cylindrical tube. The first dam 240, 350 (located within the elongated portal between the inner and outer flanges) prevents fluid from squirting out of the body when instruments are being inserted through the cannula. The second dam 320 (located at the outer, top flange) prevents fluid from squirting when the cannula itself is being inserted within the body.

With advancement of the cannula 100, 200, 300 through the cylindrical tube, the inner deformable flange flips open against the inner wall. Once the tube is removed, the outer deformable flange flips open against the patient's skin. In this manner, an optimized cannula with flanges under and over tissue, and with dams for preventing fluid leakage, for maximized tissue retention is obtained.

The present invention also provides a method of conducting minimally invasive surgery by: (i) providing a flexible button cannula 100, 200, 300 having two radially expanding deformable flanges designed to pass through a corresponding surrounding sleeve, and to flip open to engage the inner and outer surface of a body wall, and a first and second dam for preventing fluid from squirting out of the body; and (ii) conducting at least one surgical procedure employing the cannula 100, 200, 300.

The button cannulas 100, 200, 300 described in connection with exemplary embodiments of the invention may also be of varying and different shapes and lengths depending upon the application or surgical procedure. Further, to the extent a given button cannula is longer than needed, spacer(s) may be used to create a better fit within the body portal and to optimize stability of the cannula.

Button cannulas 100, 200, 300 of the present invention may be formed as a single piece, clear cannula and may be preferably formed of an elastomeric, tissue-compatible material such as silicone, for example, or combination of elastomeric or similar materials (with additional colorants, if desired).

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A cannula for enabling passage of surgical instruments through a portal passing through tissue, comprising:
   an elongated, cylindrical flexible body of constant diameter having a first end and an opposing second end, and a longitudinal axis;
   a first flexible flange integral with the first end, and a second flexible flange integral with the second end, so that the cannula is formed as a single piece, the first and second flexible flanges having a diameter substantially greater than the constant diameter of the cylindrical flexible body and extending substantially perpendicularly outward from the cylindrical body, the first and second flexible cylindrical flanges having substantially flat inner surfaces oriented approximately perpendicular to the longitudinal axis of the flexible body; and a substantially planar flexible membrane disposed within the elongated body approximately midway between the first and second flanges and oriented in a direction about perpendicular to the longitudinal axis of the elongated body, wherein upon insertion of the cannula through the portal, the first flexible flange flips open so that its substantially flat inner surface rests against one side of the tissue and the second flexible flange flips open so that its substantially flat inner surface against an opposite side of the tissue.

2. The cannula of claim 1, wherein one of the first and second flanges has a circular configuration, and wherein the other of the first and second flanges has an oval configuration.

3. The cannula of claim 1, wherein a thickness of the first flange is about equal to the thickness of the second flange.

4. The cannula of claim 1, wherein a thickness of the first flange is different from the thickness of the second flange.

5. The cannula of claim 1, wherein first flange is circular and the second flange is oval, and wherein a diameter of the first flange is about equal to the major diameter of the second flange.

6. The cannula of claim 1, wherein the flexible membrane further comprises a dam configured to prevent fluid from squirting out of the body when surgical instruments are being inserted through the cannula.

7. The cannula of claim 6, wherein the dam is in the shape of a slit in the flexible membrane.

8. The cannula of claim 1, wherein one of the first and second flanges further comprises another flange securely affixed to the one of the first and second flanges.

9. The cannula of claim 8, wherein the another flange is provided with a circular dam.

10. The cannula of claim 9, wherein the circular dam is an opening for preventing fluid from squirting from within the body during insertion of the cannula itself into the body.

11. The cannula of claim 1, wherein at least one of the elongated body, the first flange and the second flange is formed of an elastomeric material.

12. The cannula of claim 1, wherein at least one of the elongated body, the first flange and the second flange is formed of silicone.

* * * * *